United States Patent [19]

Takahashi et al.

[11] Patent Number: 4,840,183

[45] Date of Patent: Jun. 20, 1989

[54] ELECTROCARDIOGRAPH

[75] Inventors: Minoru Takahashi, Funabashi; Tsutomu Kotani, Kamagaya, both of Japan

[73] Assignee: TDK Corporation, Tokyo, Japan

[21] Appl. No.: 225,224

[22] Filed: Jul. 28, 1988

[51] Int. Cl.$^4$ .............................................. A61B 7/04
[52] U.S. Cl. ..................... 128/715; 381/67; 381/177
[58] Field of Search ............... 128/715, 773, 639–641, 128/739, 695–696, 687; 381/67, 177; 181/158, 160; 324/247

[56] References Cited

U.S. PATENT DOCUMENTS

| | | | |
|---|---|---|---|
| 2,311,416 | 2/1943 | Salb et al. | 128/715 |
| 2,583,941 | 1/1952 | Gordon, Jr. | 128/715 X |
| 3,555,187 | 1/1971 | Rowley | 128/715 |
| 3,867,925 | 2/1975 | Ersek | 128/715 |
| 4,458,687 | 7/1984 | Dickson | 128/715 X |
| 4,765,321 | 8/1988 | Mohri | 128/715 |
| 4,805,633 | 2/1989 | Kotani et al. | 128/715 |

FOREIGN PATENT DOCUMENTS

| | | | |
|---|---|---|---|
| 0120707 | 10/1984 | European Pat. Off. | 128/715 |
| 2120901 | 12/1983 | United Kingdom | 128/715 |

Primary Examiner—Kyle L. Howell
Assistant Examiner—Angela D. Sykes
Attorney, Agent, or Firm—Burgess, Ryan & Wayne

[57] ABSTRACT

A displacement sensor for an electrocardiograph attaches a permanent magnet chip directly on a living body, and movement or vibration of the living body is sensed by measuring flux by said magnet. The electrocardiograph has a magnet assembly having an adhesive film mounting a permanent magnet at the center of the film supported on a bottom ring which has a plurality of upright walls with jaws, for detachably engaging the magnet assembly with a sensor body. The sensor body has saturable inductors which are placed in flux by said magnet and are coupled with a process circuit having an astable multivibrator with a collector load by said saturable inductors and a low-pass filter connected to the output of the multivibrator. The magnet assembly is first adhered on a living body, then, the sensor body is engaged with the same by engaging said jaws with a projection on the sensor body, then, the process circuit provides an output signal reflecting the movement of a living body. Said jaw on the sensor body and/or the magnet assembly has a slanted surface for easy coupling and/or detachment of the sensor body and the magnet assembly. Said adhesive film is covered with a removable paper, which is removed when the device is used. The length between said permanent magnet and said saturable inductors is set a little longer than the desired length for operation, taking into consideration the convexed profile of a human body.

7 Claims, 9 Drawing Sheets

Fig. IIA

Fig. IIB

Fig. IIC

ELECTROCARDIOGRAPH

The present invention is the continuation-in-part application based upon U.S. patent application Ser. No. 140,043 filed Dec. 31, 1987, now U.S. Pat. No. 4,805,633.

BACKGROUND OF THE INVENTION

The present invention relates to an electrocardiograph, and in particular, relates to such a device which senses the displacement or vibration of a living body. The present invention is applicable to a stethoscope for medical and mechanocardiogram purposes.

Conventionally, an acoustic stethoscope has been used for diagnosing the internal conditions of a living body. A prior stethoscope places a diaphragm on a surface of a living body, and the vibration of the diaphragm is listened to by a doctor through a stethoscope tube.

Therefore, a prior stethoscope has the disadvantage that only a single doctor can listen to the sound of the vibration of the heart valves of a living body, but it cannot be listened to by a plurality of persons. Further, a prior stethoscope has the disadvantage that a doctor cannot listen to the sound of a heart beat with a frequency less than 20 Hz, and the output of the stethoscope cannot be recorded.

On the other hand, a prior electrocardiograph records a pulsation or electrical drive signal of a heart, but it does not record the actual mechanical movement of a heart. Therefore, if there is something wrong with a heart, such as valve disease and arteriosclerosis, it could not be detected by a prior electrocardiogram. Conventional mechanocardiograph sensors for detection of heart movement have a disadvantage due to their difficulty in usage.

Figure 1:
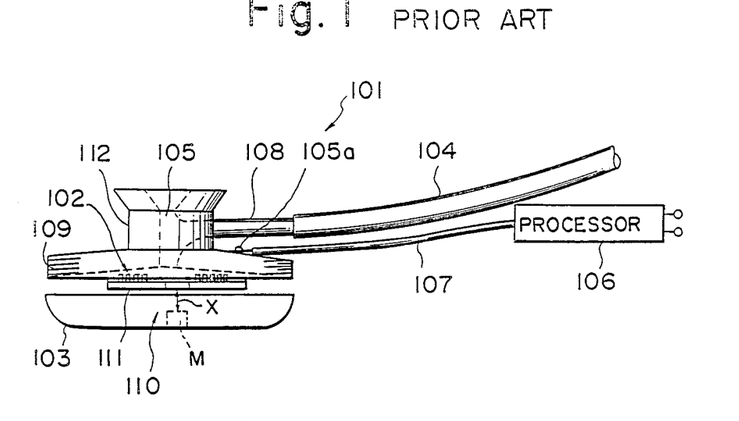
FIG. 1 shows a structure of a prior displacement sensor.

The present applicant proposed an improved displacement sensor as shown in FIG. 1, which solves the above problem, in U.S. patent application Ser. No. 931,699, now U.S. Pat. No. 3,765,321 and EP Patent publication No. 0228178. The displacement sensor of FIG. 1 uses the principle of inductance control by a movable permanent magnet.

In the figure, the displacement sensor for the stethoscope 101 has a main body 112, a diaphragm 103 and a sensor 110.

A hollow rigid tube 108 is coupled with the main body 112, and a flexible tube 104 is coupled with said hollow rigid tube 108. Accordingly, an acoustic vibration in empty space 105 in the main body 112 propagates through the rigid tube 108 to the flexible tube 104, the far end of which is to be inserted into the ear of a doctor. The main body 112 has a screw 109 at the outer surface of the same, and the diaphragm 103 is engaged with that screw. The sensor 110 is mounted between the diaphragm 103 and the main body 112.

The sensor 110 functions to generate an electrical signal according to the vibration of the diaphragm 103, and said sensor 110 has a magnetic pole M (a small permanent magnet), a group of inductors 102 which cause inductance variation according to displacement of said magnetic pole M, and a holder 111 for fixing the inductors 102. The sensor terminal 105a is mounted on the main body 112 so that the lead wires of said inductors 112 are coupled with the sensor cable 107 through the sensor terminal 105a. The far end of the sensor cable 107 is coupled with a processor 106 which processes the signal from the sensor 110.

Accordingly, the stethoscope of FIG. 1 functions both as a prior stethoscope which propagates acoustic vibration to an ear, and as an electric stethoscope which provides electrical output information according to the vibration of the diaphragm 103.

However, we realized some problems of the stethoscope of FIG. 1. First, some noise is induced on cable 107, because the processor circuit 106 is separated from the stethoscope 101. Furthermore, we realized that it does not need to double as an acoustic stethoscope. More importantly, to put the stethoscope accurately on an affected part of a living body for a long time is difficult. Also, since the stethoscope of FIG. 1 is applied on an affected part by a doctor's hand, the electrical output depends upon the pressure put by the stethoscope on an affected part.

Figure 2:
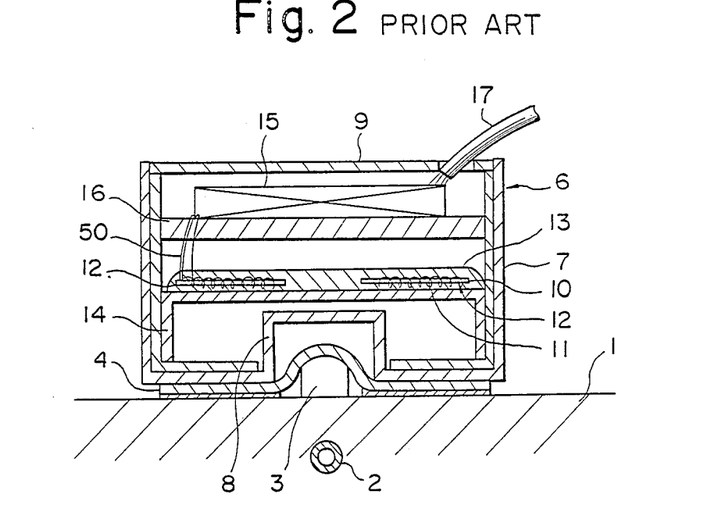
FIG. 2 shows another structure of a prior displacement sensor.

In order to solve the above problems, we made the first step with a displacement sensor as shown in FIG. 2, which uses the same electrical principle as that of FIG. 1, but a processor circuit is included in the stethoscope head, the acoustic stethoscope is removed, and the stethoscope is adhered to an affected part of a living body instead of applying the same by hand.

In FIG. 2, a permanent magnet 3 is put on an affected part 2 of a living body 1 by an adhesive thin film 4. The sensor body 6 has a recess 8 at the bottom of the housing 7. The sensor body 6 is put on the affected part so that the permanent magnet 3 is within the recess 8. The non-magnetic conductive shield case 9 is inserted in the housing 7, and an even number of inductors 12 each having a magnetic wire 10 and a coil 11 wound on the wire 10 are arranged radially with an equal angular interval. The inductors are molded on the inductor shelf 14 by plastics 13. The printed circuit board 16 which mounts a processor circuit 15 is positioned on the inductor shelf 14 with some spacing. A lead wire 17 connects the process circuit 15 with an external circuit. The numeral 50 is a lead wire connecting the inductors 12 to the processor circuit 15.

However, we found experimentally that the structure of FIG. 2 has the disadvantage that it is difficult to locate the sensor body 6 so that the center of the recess 8 coincides with the center of the permanent magnet 3. It should be noted that the diameter of the magnet is about 4 mm, and the inner diameter of the recess 8 is about 10 mm so that the magnet 3 can vibrate freely in the vertical direction. The locational error of the sensor body 6 causes the error of an output signal of the displacement sensor, and/or deteriorates the essential sensitivity of the sensor.

SUMMARY OF THE INVENTION

It is an object, therefore, of the present invention to overcome the disadvantages and limitations of a prior stethoscope and/or a prior displacement sensor by providing a new and improved electrocardiograph which is used as a stethoscope.

It is also an object of the present invention to provide an electrocardiograph which includes a processor circuit, and is free from the positioning error of a permanent magnet.

It is also an object of the present invention to provide an electrocardiograph which is put on an affected part of a living body without manually applying pressure with a hand.

The above and other objects are attained by an electrocardiograph having; a sensor body having a substrate (16), a plurality of saturable inductors connected alternately in series mounted on one surface of said substrate radially with a predetermined angular period, each of said saturable inductors having a saturable magnetic core and a coil wound on the core, a process circuit (15) for processing output of said saturable inductors mounted on the other surface of said substrate, a lead wire coupled with said process circuit for supplying power to said process circuit and obtaining output of the process circuit, a shield case (31) surrounding said process circuit, and a housing (32) for securing above members having a projection (32b) on the external wall of the housing; a magnet assembly having a bottom ring (38a) with a plurality of upright wall chips (41) positioned perpendicularly at periphery of said bottom ring, a film (39) having a permanent magnet (3) at center of said film attached to said bottom ring, each of said wall chips having jaws at the extreme end so that said jaw engages detachably with said projection (32b) of the housing (32), and plurality of posts (43) fixed to said bottom ring (38) so that it touches with said sensor body when it is engaged with the magnet assembly, and said magnet is positioned close to said saturable inductors; and at least one of said jaw (141a) on the wall (41) and said projection (32b) on said housing (32) has a slanted surface which engages with said projection (32b) or said jaw (141a).

BRIEF DESCRIPTION OF THE DRAWINGS

The foregoing and other objects, features, and attendant advantages of the present invention will be appreciated as the same become better understood by means of the following description and accompanying drawings wherein.

DESCRIPTION OF THE PREFERRED EMBODIMENTS

Figure 3:
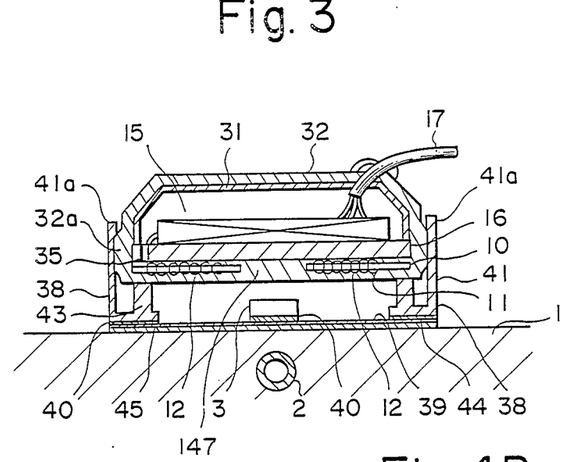
FIG. 3 shows a cross section of an electrocardiograph according to the present invention.
Figures 4A, 4B:
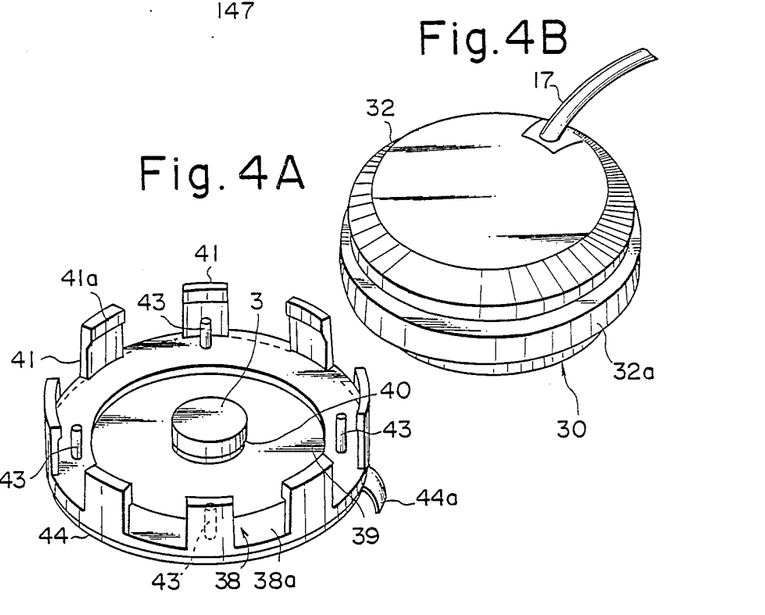
FIGS. 4A and 4B show perspective view of the electrocardiograph according to the present invention.
Figure 5:
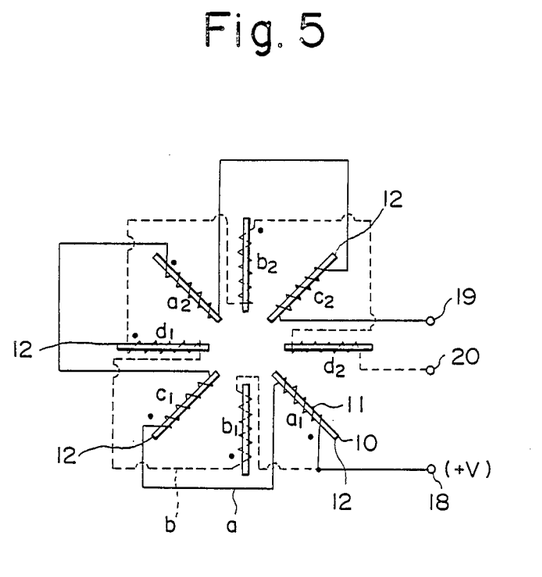
FIG. 5 shows arrangement of the coils of the electrocardiograph according to the present invention.

The electrocardiograph according to the present invention is now described in accordance with FIGS. 3, 4A and 4B. In those figures, the numeral 16 is a substrate. On one surface of the substrate 16 which faces with a permanent magnet 3, an even number of inductors 12 each having a saturable magnetic wire 10 made of amorphous material and a coil 11 wound on the wire 10 are located radially as shown in FIG. 5. The inductors 12 are positioned radially with a predetermined angular interval as shown in FIG. 5. On the other side of the substrate 16, the process circuit 15 which processes an output signal of the inductors 12 is mounted. The process circuit 15 is shielded by a non-magnetic conductive case 31 made of bronze or aluminium. The lead wire 17 is connected to the process circuit 15 for an external connection. The housing 32 is obtained by molding the inductors 12, the substrate 16 and the shield case 31 which is attached inside of the housing 32 by using dielectric plastics. Thus, the sensor body 30, which has the above structure, is obtained. It should be noted that the inductors 12 and the shield case 31 are fixed temporarily on the substrate 16 by using adhesive, when the molding process is carried out for preventing positional error of the members during the molding process. The numeral 35 is a hole in which a wire connecting the element 12 to the circuit 15 passes.

The numeral 38 is a circular frame made of plastics, which mounts the permanent magnet 3, and is detachably engaged with the sensor body 30. The frame 38 has a bottom ring 38a, a circular flexible non-magnetic adhesive film 39 which is adhered to the bottom ring 38a through the plastics adhesive 40. The permanent magnet chip 3 is fixed at the center of the film 39 through the plastics adhesive 40. The film 39 is preferably thin so that it does not disturb the movement of a living body, and is transparent. A non-woven fabric which has uniform expansion property in all the directions is preferably used as said film 39.

The frame 38 has a plurality of upright walls 41, each of which has a projected jaw 41a at the end of the wall 41 so that the jaw 41a engages detachably with the ring 32a which is projected on the outer surface of the housing 32 as shown in FIG. 3. Preferably, more than four walls 41 are provided. The bottom ring 38a has a plurality of bars 43 with a predetermined angular distance so that said bar 43 functions as a stopper to position the frame 38 when the frame 38 is engaged with the housing 32. The numeral 44 is a non-adhesive cover which is attached on the surface of said adhesive film 39.

In operation, it should be noted that the magnet assembly of FIG. 4A is, first, separated from the sensor body of FIG. 4B.

The cover 44 is removed, so that the adhesive 45 on the film 39 appears, then, the magnet assembly is adhered on a skin 1 of a living body so that the permanent magnet 3 locates on an affected part. When the film 39 is transparent, the magnet is accurately positioned on an affected part. Next, the sensor body 30 is engaged with the frame assembly.

It should be appreciated that when the magnet assembly is engaged with the sensor body 30, the magnet 3 is positioned at the center of the inductors group 12, since the rear surface of the housing 32 contacts with the top of the bars 43, and the frame 38 is resiliently engaged with the ring 32a by the resilient property of the material of the walls 41.

It should be appreciated that the sensor body 30 is engaged with and/or detached from the magnet assembly with only a slight resistance, since the walls 41 are separated into a plurality of chips.

The electrical operation of the present displacement sensor is similar to that of the U.S. patent application Ser. No. 931,699 (EP patent publication No. 0228178, and U.S. patent application No. 881,110.

The inductors 12 are saturable inductors having an amorphous core, and the inductors 12 are positioned radially as shown in FIG. 5. The inductors 12 are connected alternately in series as shown in FIG. 5, so that the inductors $a_1$, $c_1$, $a_2$, and $c_2$ are connected in series, and the inductors $b_1$, $d_1$, $b_2$ and $d_2$ are connected in series. Only a pair of inductors (for instance, $a_1$ and $a_2$), would be enough for merely sensing the magnetic field, but the radially positioned arrangement and the alternate series connection as shown in FIG. 5 allow it to get rid of the influence of the earth's magnetism.

The amorphous wire 10 of the inductors for instance has the composition $Co_{68}Fe_4Si_{13}B_{15}$ in atomic percent, and the diameter is 110 μm, and the length is 3 mm, in one embodiment.

Figure 6:
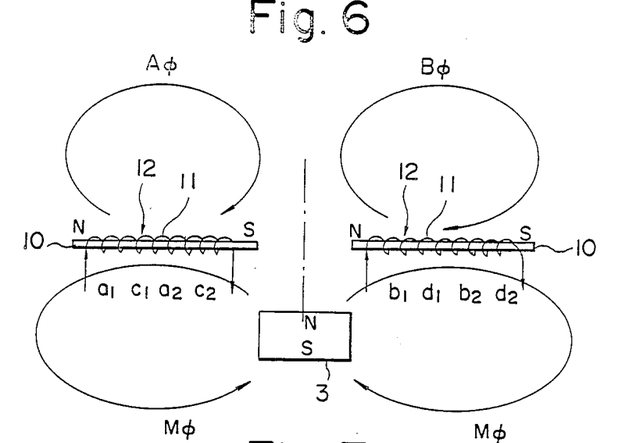
FIG. 6 shows the operation of the inductors according to the present invention.

It should be noted that the total inductance of the first serially connected inductors ($a_1$, $c_1$, $a_2$, $c_2$) differs from that of the second serially connected inductors ($b_1$, $d_1$, $b_2$, $d_2$) which are shown by a dotted line, depending upon the position of the permanent magnet 3. FIG. 6 shows that situation.

In FIG. 6 where the magnet 3 has the north pole N close to the inductors 12, the magnetic flux $M_\phi$ by the magnet 3 is cancelled by the flux $B_\phi$ by the current in the coil 11 as shown in right half of FIG. 6. On the other hand, the flux $M_\phi$ by the magnet 3 is added to the flux $A_\phi$ by the current in the coil 11. When the flux by the magnet is in the same direction as that of the current, the magnetic core 10 would be saturated.

Thus, the inductance of the first serially connected inductors differs from that of the second serially connected inductors. And, the difference of the inductance between two serially connected inductors depends upon the position of the permanent magnet 3. Thus, the position or the vibration of the permanent magnet is sensed by measuring the inductance difference.

Figure 7:
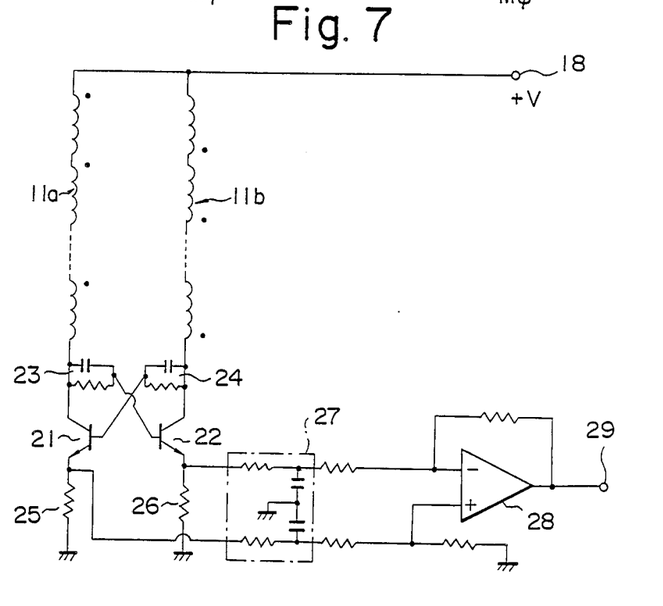
FIG. 7 shows the process circuit of the electrocardiograph according to the present invention.

The inductance difference is measured by the process circuit. FIG. 7 is the embodiment of the process circuit, which is essentially an astable multivibrator.

One end of the first serially connected coils 11a and the second serially connected coils 11b are commonly coupled with the power source 18 (+V), and the other ends of those coils are connected to the collectors of the transistors 21, and 22, respectively. The emitters of those transistors are grounded through the resistors 25 and 26, respectively. The parallel circuits 23 and 24 each having a resistor and a capacitor connect the base and the collector of the transistors. The emitters of the transistors are connected to the low-pass filter 27 (integration circuit, the output of which is coupled with the DC amplifier 28, which provides the displacement output 29.

It should be noted that the oscillation period of an astable multivibrator depends upon the inductance connected to the collector. Since that inductance depends upon the location of the magnet, the half period of the oscillation of the astable multivibrator depends upon the location of the magnet. The low-pass filter 27 attenuates the AC component of the astable multivibrator, and provides only the DC component, which reflects the location of the permanent magnet.

Figure 8:
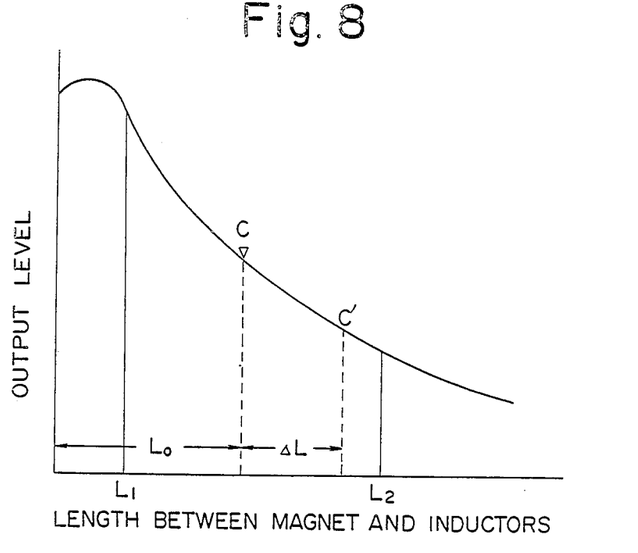
FIG. 8 and FIG. 9 show operational curves of the electrocardiograph according to the present invention.

FIG. 8 shows the curve between the location of the magnet (horizontal axis), and the output voltage at the terminal 29. It should be noted that the curve has an essentially linear portion when the location of the magnet is between $L_1$ and $L_2$. Therefore, the system is designed so that the magnet is positioned at the center C of the linear portion. The oscillation frequency of the astable multivibrator is, preferably, in the range between 100 kHz and 500 kHz. The time constant of the electrocardiograph, or the quickness of the response of the sensor depends upon the time constant of the low-pass filter 27. Therefore, that low-pass filter is designed according to the velocity of the movement of the object to be sensed.

Figure 9:
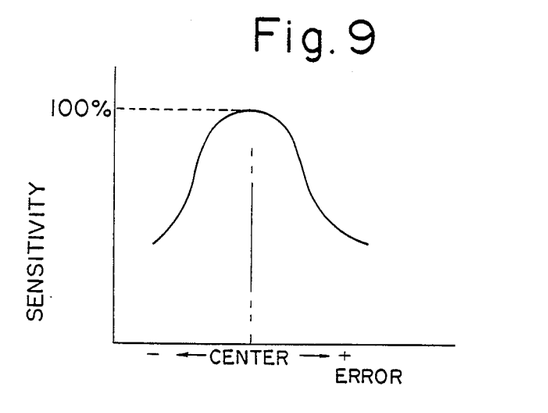

FIG. 9 shows the curve between the sensitivity (vertical axis) and the locational error of the permanent magnet (horizontal axis). The sensitivity is of course the maximum when the error is zero, or the magnet is positioned at the center of the inductors. When the magnet has the positional error, the sensitivity decreases as shown in FIG. 9. It should be appreciated that the positional error of the magnet according to the present invention is very small, as compared with that of a prior art of FIG. 1 or FIG. 2, since the magnet is attached on the center of the magnet assembly, which is coupled detachably with the sensor body by using a snap action of upright walls.

Thus, the movement of an affected portion of a living body is sensed by the movement of the permanent magnet, and the movement of the permanent magnet is sensed by the inductance difference, which is measured by the process circuit. Thus, the process circuit provides the output signal depending upon the movement of a living body.

Some modifications are of course possible to those skilled in the art. For instance, walls 41 with a jaw 41a may be mounted to a sensor body, instead of a magnet assembly. In that case, the magnet assembly has a ring corresponding to the ring 32a for engaging with the jaws.

Figure 10:
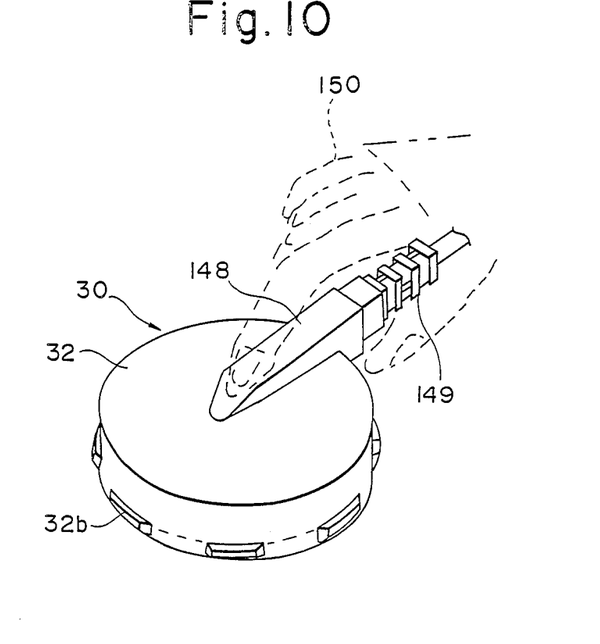
FIG. 10 shows a modified structure of the electrocardiograph according to the present invention.

FIG. 10 shows a modification of the present invention, and the feature of the modification of FIG. 10 is that the projection 32b on the sensor body 30 is not a continuous ring, but a plurality of chips positioned on a ring with a predetermined interval. Further, the modification of FIG. 10 has a solid wire holder 148 on the sensor body 30, and the solid extension 149 for holding the wire. The numeral 150 is a hand of an inspector. The sensor holder 30 is held by the hand 150 with the wire holder 148 and the extension 149 of the wire holder.

Figure 11A:
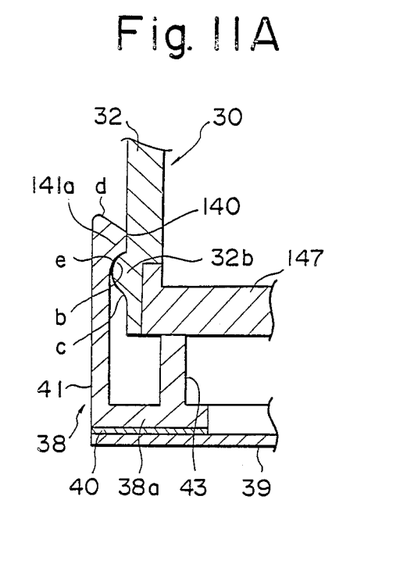
FIGS. 11A, 11B, and 11C show some embodiments of the detailed structure of the coupling between the magnet assembly and the sensor body.
Figure 11B:
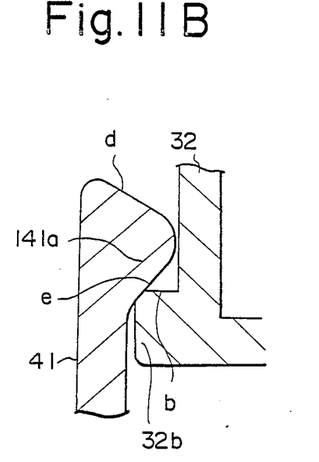
Figure 11C:
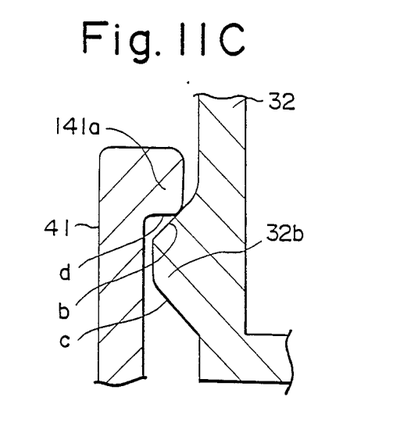

FIG. 11A through 11C show some modifications of the structure for engaging the sensor body 30 with the magnet frame 38. The same numerals in those figures show the same members as those in FIGS. 3 and 4, and the numeral 141a is a jaw on the wall 41, and 32b is a projection on the sensor body 30.

In the modification of FIG. 11A, the jaw 141a on the wall 41 has a slanted upper surface d and the downwardly slanted surface e. Similarly, the projection 32b on the sensor body 30 has an upwardly slanted surface b and the downwardly slanted surface c. As shown in FIG. 11A, the jaws 141a and the projections 32b are engaged with each other by contacting the lower surface e of the jaw 141a with the upper surface b of the projection 32b. The height of the bar or post 43 is designed so that the post 43 touches with the bottom of the sensor body 30 when the jaws projections 141a and the projections 32b just engage.

FIG. 11B is another modification of the engagement. In this modification, the upper surface b of the projection 32b is not slanted, but is flat and parallel with the bottom surface of the frame 38.

FIG. 11C is another modification of the engagement. In this modification, the down surface of the jaw 141a is not slanted but is flat and parallel to the bottom surface of the frame 38.

It should be appreciated in FIGS. 11A through 11C that at least one of said jaw 141a on the wall 41 and said projection 32b on side of said housing 32 has a slanted surface. The slanted surface facilitates the coupling and the detachment of the sensor body and the magnet assembly.

In the modifications of FIGS. 11B and 11C, the slanted surface of a projection or a jaw engages with a horizontal surface of a jaw or a projection. Since the manufacturing process of a horizontal projection or a jaw is easier than that of a slanted projection or a slanted jaw, the producing cost in FIGS. 11B and 11C is lower than that of that of FIG. 11A, without decreasing the operational reliability of the device.

Figure 12:
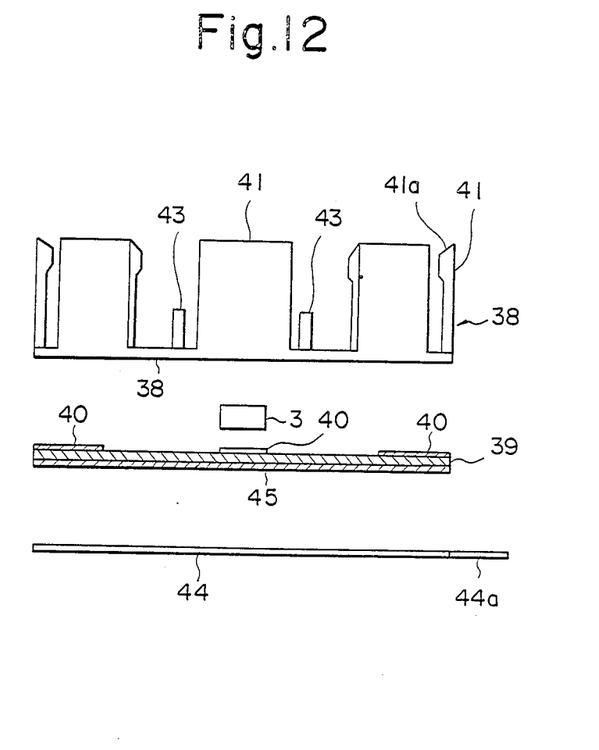
FIG. 12 shows the detailed structure of the magnet assembly.

FIG. 12 shows the enlarged view of the magnet assembly. In the figure, the numeral 38 is a frame, 39 is a film, 40 is an adhesive, 41 is a wall, 41a is a jaw on the wall 41, 45 is an adhesive. The numeral 44 is removable paper which is adhered to the film 39 by the adhesive 45. The numeral 44a is an extension tongue of the removable paper 44. The extention tongue 44a is used to remove the paper 44 from the film 39. The magnet 3 is adhered on the film 39 by the adhesive 40. The film 39 is adhered to the frame 38 by the adhesive 40. The paper 44 is removably adhered to the film 39 by the adhesive 45, and paper 44 is removed from the film 49 by drawing the tongue 44a.

Figure 13:
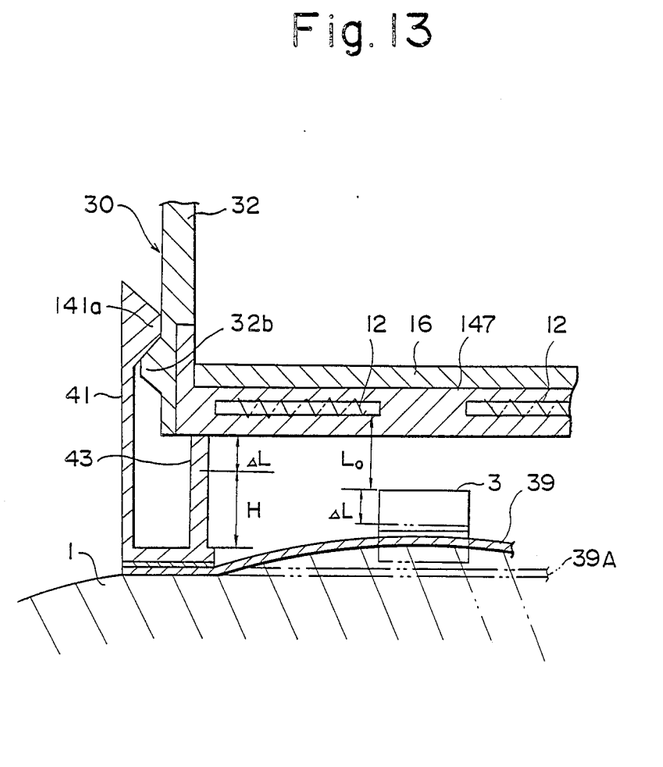
FIG. 13 shows the analysis of the length between the magnet 3 and the inductors 12.

FIG. 13 shows the practical positioning of the magnet 3.

It should be noted that the surface of a human body is generally convex. Therefore, when the length between the magnet 3 and the inductor 12 is designed so that said length is the center C of the linear portion of the operational curve of FIG. 8, the actual length between the magnet 3 and the inductors 12 is shorter than the desirable length, because of the convex profile of a human body.

In view of that fact, the present invention takes the length to be $L_0 + \Delta L$, where $L_0$ is the desirable length in operation between the magnet 3 and the inductors 12, and $\Delta L$ is the error due to the convex profile of a human body. When the present sensor is put on a human body, the magnet 3 is raised by the length $\Delta L$ by the convex profile of a human body, and then, the length between the magnet 3 and the inductors 12 becomes to be $L_0$ which the desirable length for operation of the present device.

The above adjustment of the length is implemented by designing the length of the posts 43 longer by $\Delta L$ than the desirable length H in which no convex profile is considered. So, when the present device is not placed on a human body, the operational point is C' in FIG. 8, and when the present device is put on a human body, the operational point shifts to C in FIG. 8 due to the convex profile of a human body.

In one numerical embodiment, the length $L_0$ is 2.5 mm, and the length $\Delta L$ is 0.5 mm, and the diameter of the frame 38 is 30 mm.

From the foregoing, it will now be apparent that a new and improved electrocardiograph or displacement sensor has been found. It should be understood of course that the embodiments disclosed are merely illustrative and are not intended to limit the scope of the invention. Reference should be made to the appended claims, therefore, rather than the specification as indicating the scope of the invention.

What is claimed is:

1. An electrocardiograph comprising:

a sensor body having a substrate (16), a plurality of saturable inductors connected alternately in series mounted on one surface of said substrate radially with a predetermined angular period, each of said saturable inductors having a saturable magnetic core and a coil wound on the core, a process circuit means (15) for processing an output of said saturable inductors and mounted on the other surface of said substrate, a lead wire coupled with said process circuit for supplying power to said process circuit and obtaining an output of the process circuit, a shield case (31) surrounding said process circuit, and a housing (32) for securing the above members having a projection (32b) on an external wall of the housing, a magnet assembly having a bottom ring (38a) with a plurality of upright wall chips (41) positioned perpendicularly at a periphery of said bottom ring, a film (39) having a permanent magnet (3) at a center of said film attached to said bottom ring, each of said wall chips having an extreme end and jaws at the extreme end so that each said jaw engages detachably with said projection (32b) of the housing (32), and a plurality of posts (43) fixed to said bottom ring (38) so that it touches with said sensor body when it is engaged with the magnet assembly, and said magnet is positioned close to said saturable inductors, wherein the improvements comprise in that at least one of said jaws (141a) on the wall chips (41) and said projection (32b) on said housing (32) has a slanted surface which engages with said projection (32b) or said jaw (141a).

2. An electrocardiograph according to claim 1, wherein said jaw (141a) has a slanted upper surface (d) and a slanted down surface (e), and said projection (32b) has a slanted upper surface (b) and a slanted lower surface (c).

3. An electrocardiograph according to claim 1, wherein said jaw (141a) has a slanted upper surface (d) and a slanted lower surface (e), and said projection (32b) has a horizontal upper surface (b).

4. An electrocardiograph according to claim 1, wherein said jaw (141a) has a horizontal lower surface (d), and said projection (32b) has a slanted upper surface (b) and a slanted lower surface (c).

5. An electrocardiograph according to claim 1, wherein a paper (44) having an extension tongue (44a) is removably adhered to said film (39).

6. An electrocardiograph according to claim 1, wherein the process circuit means has an operational curve with a linear portion and a center of the linear portion, and the length of said posts (43) is longer by $\Delta L$ than length (H) which locates said magnet (3) to the center (C) of the linear portion of the operational curve of said process circuit means.

7. An electrocardiograph according to claim 6, wherein said length $\Delta L$ is 0.5 mm.

* * * * *

UNITED STATES PATENT AND TRADEMARK OFFICE
CERTIFICATE OF CORRECTION

PATENT NO. : 4,840,183
DATED : June 20, 1989
INVENTOR(S) : Minoru Takahashi, et al It is certified that error appears in the above-identified patent and that said Letters Patent is hereby corrected as shown below:

On the title page, in the first column, under "[22] Filed: Jul. 28, 1988" insert --[30] Foreign Application Priority Data

| August 13, 1987 | Japan | 62 124044 |
| August 13, 1987 | Japan | 62 124047 |
| August 13, 1987 | Japan | 62 124049 -- |

Signed and Sealed this

Twentieth Day of February, 1990

*Attest:*

JEFFREY M. SAMUELS

*Attesting Officer*     *Acting Commissioner of Patents and Trademarks*